(12) United States Patent
Rothermel et al.

(10) Patent No.: US 11,559,407 B2
(45) Date of Patent: Jan. 24, 2023

(54) WRIST IMPLANTS

(71) Applicant: The Penn State Research Foundation, University Park, PA (US)

(72) Inventors: Shane Rothermel, Hummelstown, PA (US); Scott Tucker, Elizabethtown, PA (US)

(73) Assignee: The Penn State Research Foundation, University Park, PA (US)

( * ) Notice: Subject to any disclaimer, the term of this patent is extended or adjusted under 35 U.S.C. 154(b) by 212 days.

(21) Appl. No.: 17/043,976

(22) PCT Filed: Mar. 29, 2019

(86) PCT No.: PCT/US2019/024769
§ 371 (c)(1),
(2) Date: Sep. 30, 2020

(87) PCT Pub. No.: WO2019/191549
PCT Pub. Date: Oct. 3, 2019

(65) Prior Publication Data
US 2021/0113345 A1    Apr. 22, 2021

Related U.S. Application Data

(60) Provisional application No. 62/650,413, filed on Mar. 30, 2018.

(51) Int. Cl.
*A61F 2/42*    (2006.01)
*A61F 2/30*    (2006.01)

(52) U.S. Cl.
CPC .. *A61F 2/4261* (2013.01); *A61F 2002/30242* (2013.01); *A61F 2002/30383* (2013.01); *A61F 2002/30635* (2013.01); *A61F 2002/30639* (2013.01); *A61F 2002/30831* (2013.01); *A61F 2002/4264* (2013.01)

(58) Field of Classification Search
CPC ...................... A61F 2/4261; A61F 2002/4264
See application file for complete search history.

(56) References Cited

U.S. PATENT DOCUMENTS

| 3,506,982 A | 4/1970 | Steffee |
| 3,837,008 A | 9/1974 | Bahler |
| 4,003,096 A | 1/1977 | Frey |
| 4,229,841 A | 10/1980 | Youm |
| 4,932,969 A | 6/1990 | Frey |

(Continued)

FOREIGN PATENT DOCUMENTS

| DE | 10354601 B3 * | 6/2005 | ........... A61F 2/4241 |
| EP | 808617 A2 * | 11/1997 | ............... A61F 2/32 |

(Continued)

*Primary Examiner* — Javier G Blanco
(74) *Attorney, Agent, or Firm* — Riverside Law LLP

(57) ABSTRACT

The present invention provides a prosthetic wrist implant comprising: a radial implant component having an elongated radial stem extending proximally adapted for attachment to radius, a carpal implant component having a distal surface adapted for attachment to one or more carpal bones, and a interposed component between the radial implant component and the carpal implant component that is flexible and allows for changes in orientation between the radial component and the carpal components relative to each other component.

7 Claims, 11 Drawing Sheets

(56) References Cited

U.S. PATENT DOCUMENTS

| | | | |
|---|---|---|---|
| 5,314,485 | A | 5/1994 | Judet |
| 6,007,580 | A | 12/1999 | Lehto |
| 7,625,408 | B2 | 12/2009 | Gupta |
| 2005/0085921 | A1 | 4/2005 | Gupta |
| 2009/0204223 | A1 | 8/2009 | Wolfe |
| 2010/0023126 | A1 | 1/2010 | Grotz |
| 2010/0256770 | A1 | 10/2010 | Hakansson |
| 2012/0150308 | A1 | 6/2012 | Gupta |
| 2013/0090738 | A1 | 4/2013 | Linares |

FOREIGN PATENT DOCUMENTS

| | | |
|---|---|---|
| FR | 2661817 A1 | 11/1991 |
| WO | 2017024336 | 2/2017 |

* cited by examiner

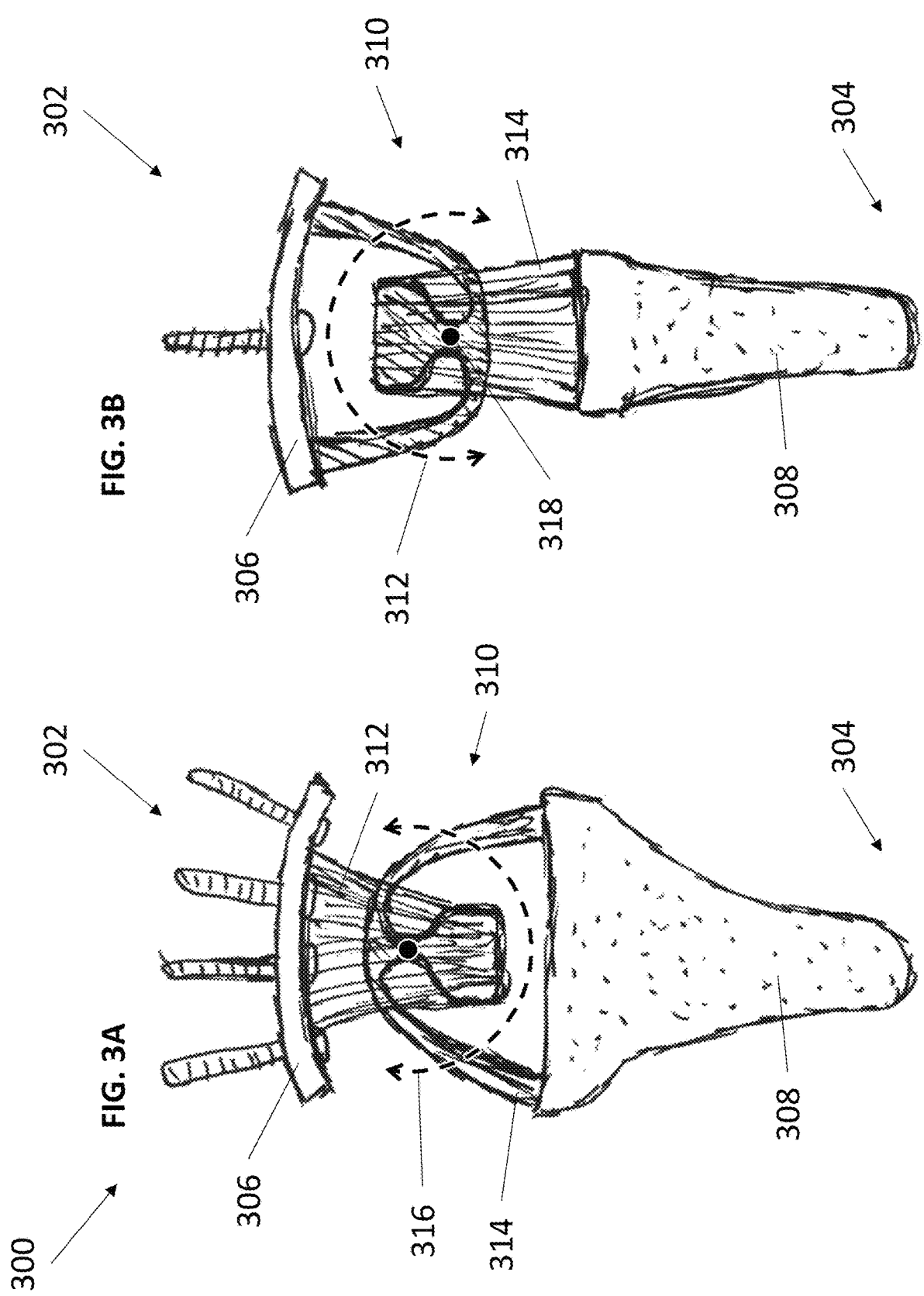

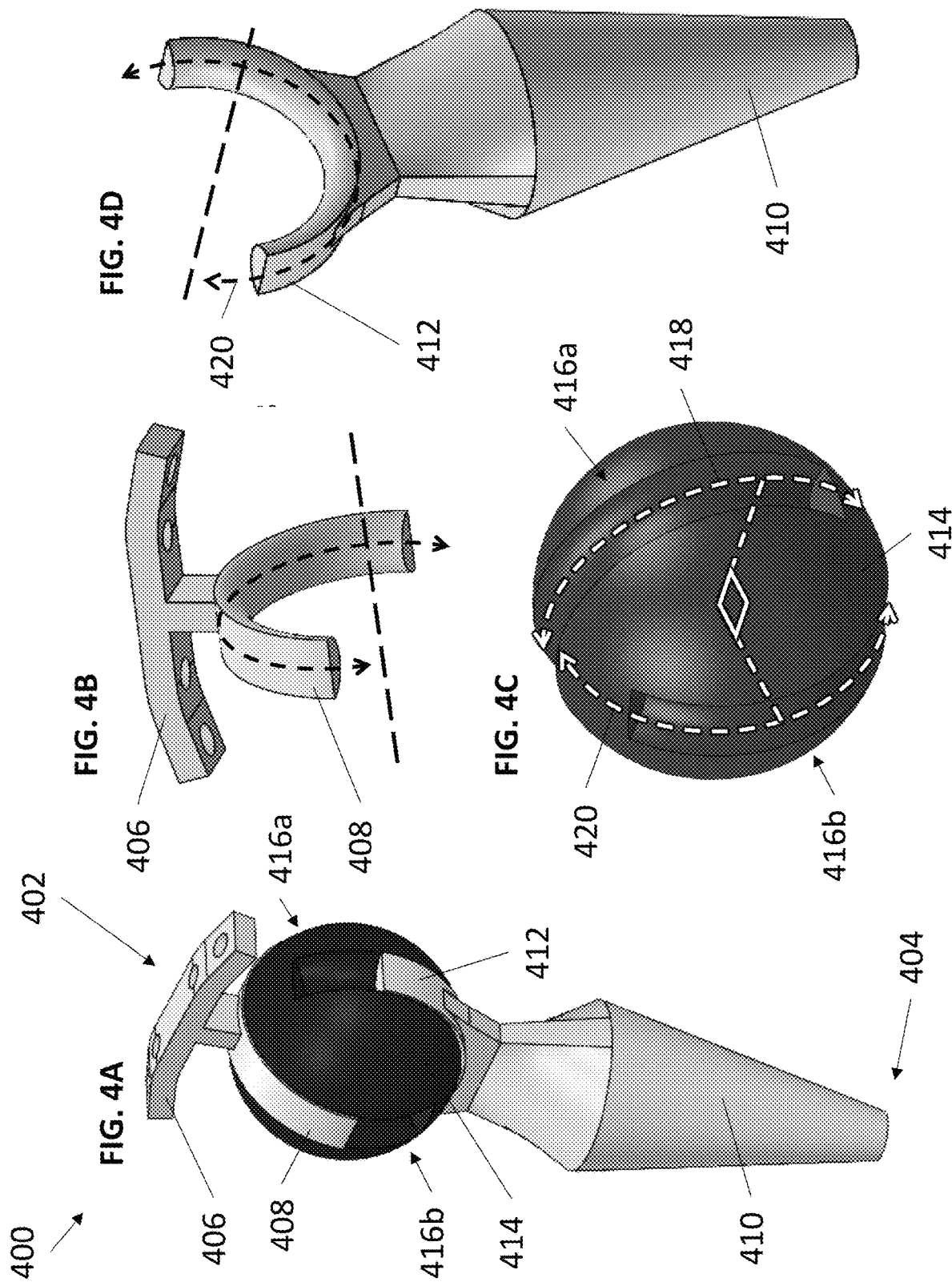

WRIST IMPLANTS

CROSS-REFERENCE TO RELATED APPLICATIONS

This application is the U.S. national phase application filed under 35 U.S.C. § 371 claiming benefit to International Patent Application No. PCT/US19/24769 filed Mar. 29, 2019, which is entitled to priority under 35 U.S.C. § 119(e) to U.S. Provisional Patent Application No. 62/650,413, filed Mar. 30, 2018, the contents of which are each incorporated by reference herein in their entirety.

BACKGROUND OF THE INVENTION

Orthopedic replacement of damaged or degenerated natural wrist joints is well known in the orthopedic arts. Prior to the introduction of a prosthetic joint replacement for the wrist, individuals suffering from a joint disease in the wrist such as radio-carpal arthritis are often surgically treated by a fusion procedure. Fusion involves repairing the injured wrist joint structures with a fixed plate or rod that stiffens the wrist. That is, the joint is fixed in position by a device that allows no movement of the wrist. While this is an improvement over a diseased or injured wrist joint, it is clearly unsatisfactory.

Existing orthopedic prostheses for wrist joint implantation have a number of limitations. Currently, most prosthetic wrist implants provide the patient with only limited functionality of the wrist, as otherwise the implant becomes unstable. A major function of the wrist is to transfer pronosupination torques from the forearm to the hand, in all positions without losing stability. This critical functional aspect of the wrist joint is overlooked in current arthroplasty designs.

It has been found that implants that allow metal to metal contact between the radial and carpal components tend to cause shedding of metal particles that may migrate into surrounding tissues and may cause tissue necrosis and consequent implant failure. Furthermore, typical metal and high molecular weight polyethylene implants succumb to wear phenomena and subsequent osteolysis and other complications.

It would be valuable for a prosthetic wrist implant to provide a secure, strong, and stable attachment to the surrounding bones in order to lower complications related to implant loosening. Further, it would be beneficial to avoid or limit metal-to-metal and metal on high molecular weight polyethylene contact between the radial and carpal components to limit wear phenomena of typical prosthetic joints with bearing surfaces. The prosthetic wrist implant of the present invention addresses the needs and limitations of current designs.

SUMMARY OF THE INVENTION

In one aspect, the present invention relates to a prosthetic wrist implant comprising: a radial component positioned proximal to a carpal component, the radial component having an elongated radial stem extending in a proximal direction configured to attach to a radius bone, and the carpal component having a distal surface configured to attach to one or more carpal bones; and an interposed component positioned between the radial component and the carpal component, the interposed component attached to the carpal component by a mobile connection rotatable about a first axis, and to the radial component by a mobile connection rotatable about a second axis, the first axis and the second axis being orthogonal to each other.

In one embodiment, the implant has a center of rotation positioned at an intersection of the first axis and the second axis. In one embodiment, the mobile connections between the interposed component, the carpal component, and the radial component are configured to rigidly support a pronosupination torque.

In one embodiment, the interposed component comprises two orthogonally intersecting axle arms. In one embodiment, the mobile connection between the interposed component and the radial and carpal components is a hinged connection. In one embodiment, the hinged connection comprises a low friction bearing. In one embodiment, the bearing is sealed.

In one embodiment, the interposed component comprises a spherical component having a first groove and a second groove embedded on an outer surface of the spherical component, the first groove being aligned along a curve of a first great-circle of the spherical component, the second groove being aligned along a curve of a second great-circle of the spherical component, and wherein a plane of the first great-circle and a plane of the second great-circle are orthogonal to each other. In one embodiment, the carpal component and the radial component each comprise a runner sized and arced to fit within and slide along the first and second grooves of the spherical component, respectively. In one embodiment, the runner of the radial component is attached to a distal plate connected to the radial component such that the runner is positioned offset from a central long axis of the radial component. In one embodiment, the offset is between about 5 mm and 25 mm.

In one embodiment, the interposed component comprises a substantially spherical component having a first groove and a second groove embedded on an outer surface of the spherical component, the first groove being aligned along a curve of a first great-circle of the spherical component, the second groove being aligned along a curve of a second great-circle of the spherical component, a plane of the first great-circle and a plane of the second great-circle are orthogonal to each other, and the first great-circle having a radius that is smaller than a radius of the second great-circle.

In another aspect, the present invention relates to a prosthetic wrist implant comprising: a radial component positioned proximal to a carpal component, the radial component having an elongated radial stem extending in a proximal direction configured to attach to a radius bone, and the carpal component having a distal surface configured to attach to one or more carpal bones; and a non-articulating interposed component comprising a first curved piece and a second curved piece, each curved piece comprising a curved length having two ends and a vertex; wherein the first curved piece is attached to the carpal component at each end, the second curved piece is attached to the radial component at each end, and the first curved piece and the second curved piece are attached to each other at their vertices.

In one embodiment, the first and second curved pieces and the attachment between the first and second curved pieces are flexible about two orthogonal axes to form a flexible interposed component configured to support flexion, extension, radial deviation, ulnar deviation, and combinations thereof. In one embodiment, the flexible interposed component is configured to support the transfer of a pronosupination torque.

In another aspect, the present invention relates to a method of implanting a prosthetic wrist implant, comprising the steps of: providing the prosthetic wrist implant of the present invention; aligning the center axis of rotation with the long axis of a patient's forearm; and positioning the center of axis of the prosthetic wrist implant near the patient's capitate bone.

In one embodiment, the prosthetic wrist implant is positioned such that an intersection of the first axis and the second axis is aligned between the proximal extent of the capitate bone and ¼ of the height of the capitate bone measured from its proximal extent. In one embodiment, the first axis is aligned orthogonally with the radial extension to volar flexion movement of the dart thrower's motion, and the second axis is aligned in parallel with the radial extension to volar flexion movement of the dart thrower's motion. In one embodiment, the first axis is aligned 45°±15° oblique from the sagittal plane of a patient's hand. In one embodiment, the first axis is aligned with the plane defined by the insertion of the flexor carpi ulnaris and the extensor carpi radialis longus/extensor carpi radialis brevis of a patient's arm.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1A depicts a prosthetic wrist implant having a carpal component and a radial component, each rotatable about orthogonal axes by way of an interposed component. FIG. 1B through FIG. 1D depicts another prosthetic wrist implant having a carpal component and a radial component, each rotatable about orthogonal axes by way of an interposed component. FIG. 1E and FIG. 1F depict the carpal component of the implant of FIG. 1B in isolation. FIG. 1G and FIG. 1H depict the radial component of the implant of FIG. 1B in isolation.

FIG. 3A and FIG. 3B depict an exemplary interposed component of the present invention. FIG. 3A depicts a front view of a non-articulating interposed component attached to a carpal component and a radial component. FIG. 3B depicts a side view of a non-articulating interposed component attached to a carpal component and a radial component.

FIG. 4A through FIG. 4D depict another exemplary prosthetic wrist implant. FIG. 4A depicts a prosthetic wrist implant having a carpal component and a radial component, each slidable about orthogonal axes by way of a channeled interposed component. FIG. 4B depicts the carpal component of the implant of FIG. 4A in isolation. FIG. 4C depicts the channeled interposed component of the implant of FIG. 4A in isolation. FIG. 4D depicts the radial component of the implant of FIG. 4A in isolation.

FIG. 5A depicts an offset prosthetic wrist implant having a carpal component and a radial component, each slidable about orthogonal axes by way of a channeled interposed component. FIG. 5B depicts the radial component of the implant of FIG. 5A in isolation. FIG. 5C depicts the channeled interposed component of the implant of FIG. 5A. FIG. 5D depicts the carpal component of the implant of FIG. 5A.

FIG. 6A depicts profile views of an exemplary prosthetic wrist implant having a first axes alignment. FIG. 6B depicts profile views of an exemplary prosthetic wrist implant having a second axes alignment.

FIG. 7A shows the results of computational mechanics using finite element analysis. FIG. 7B shows the implantation of a prototype prosthetic wrist implant in a cadaver. FIG. 7C depicts the range of motion of the implanted prosthetic wrist in the cadaver.

DETAILED DESCRIPTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides prosthetic wrist implants that solve the problems and limitations associated with current wrist prostheses. The implants minimize wear phenomena associated with current materials at articulating surfaces and allow for transfer of pronosupination torque across the wrist. The implants consist of an intersegment component between the radius portion and the carpal portion of a wrist.

Figure 1A:
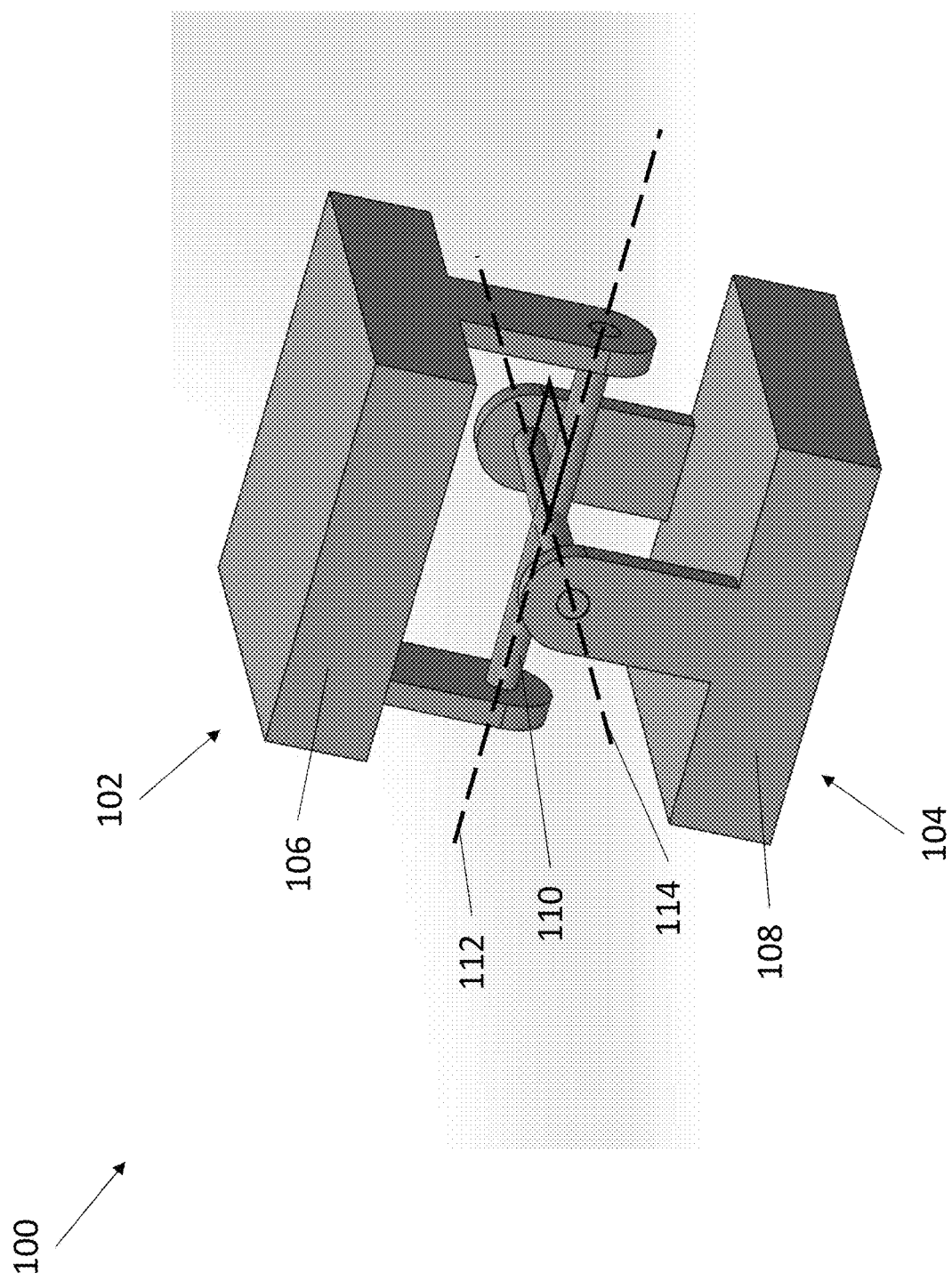
FIG. 1A through FIG. 1H depict an exemplary prosthetic wrist implant.
Figure 1D:
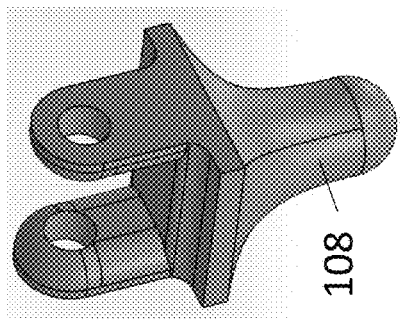
Figure 1H:
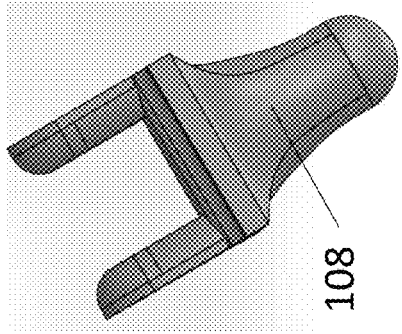
Figure 1C:
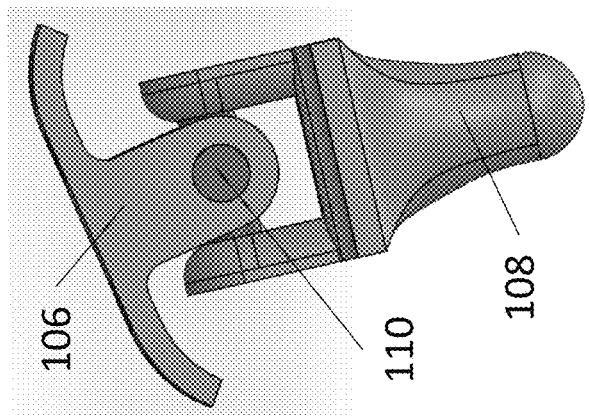
Figure 1G:
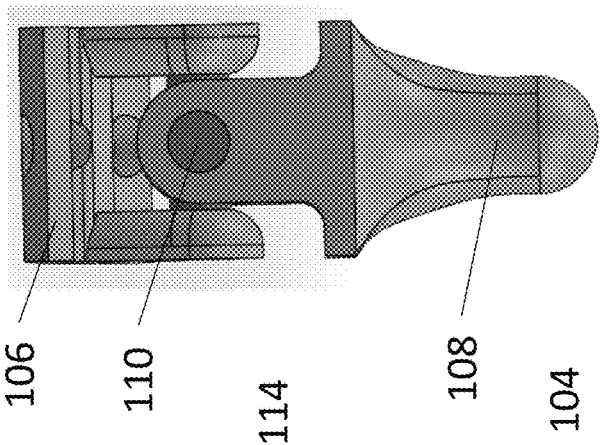
Figure 1B:
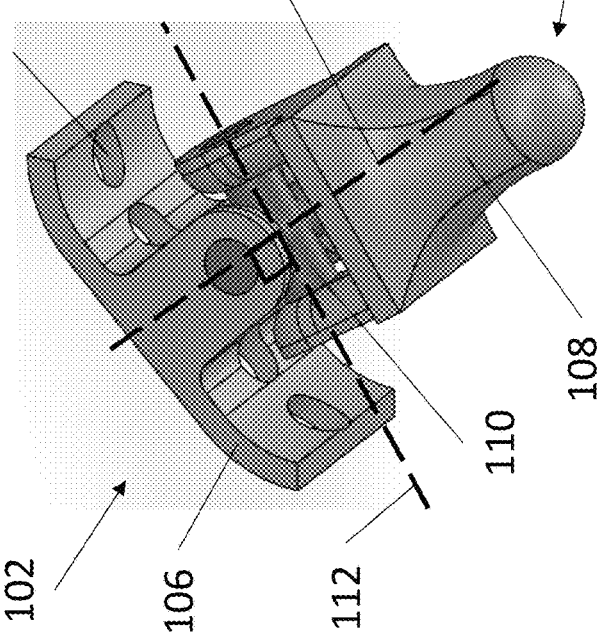
Figure 1F:
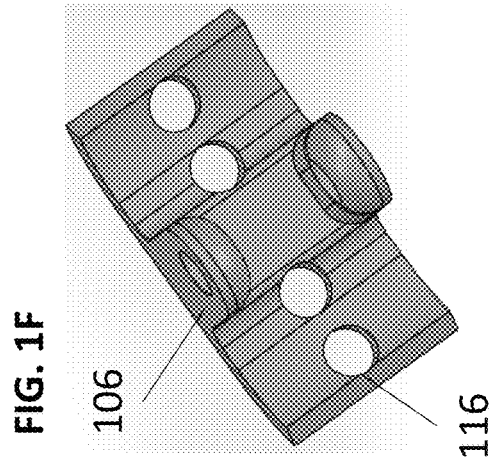
Figure 1E:
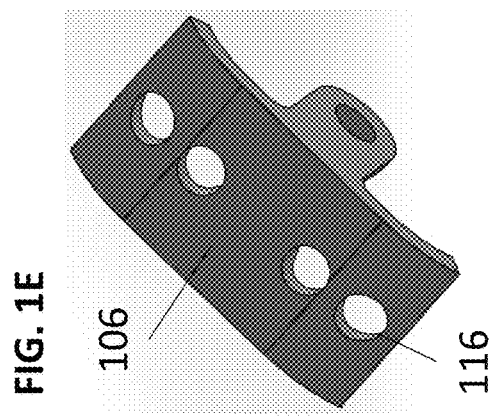

Referring now to FIG. 1A, an exemplary prosthetic wrist implant 100 is depicted. Prosthetic wrist implant 100 has a distal end 102, a proximal end 104, and comprises a carpal component 106, a radial component 108, and an interposed component 110 attached to the carpal component 106 and the radial component 108. An attachment surface is provided at the distal end of carpal component 106 and at the proximal end of radial component 108. The attachment surface can be adapted to have any suitable attachment element to join prosthetic wrist implant 100 with a wrist joint. For example, as depicted in FIG. 1B through FIG. 1H, carpal component 106 and radial component 108 can each have one or more elongated stems extending from their attachment surfaces adapted for anchoring to the carpal bones and the radial bone of a wrist, respectively. Carpal component 106 and radial component 108 can also comprise any suitable number of screw holes 116 for anchoring the components to bone or to another prosthetic structure.

Interposed component 110 is a cross-shaped piece formed from two axle arms aligned along axis 112 and axis 114. Interposed component 110 is connected to carpal component 106 by a first arm aligned along axis 112 and to radial component 108 by a second arm aligned along axis 114. Axis 112 and axis 114 are orthogonal to each other, and correspond to the wrist's extension to flexion range of motion and ulnar deviation to radial deviation range of motion, respectively. However, it should be understood that implant 100 can be implanted in any suitable orientation, such that the alignment of axis 112 and axis 114 with respect to the wrist's ranges of motion are interchangeable. In some embodiments, the connection is a hinged connection, such as by way of hinge connectors (FIG. 1A through FIG. 1D). In some embodiments, the hinged connectors can orient interposed component 110 orthogonally to carpal component 104 and radial component 106. In other embodiments, the hinged connectors can orient interposed component 110 offset from carpal component 104 and radial component 106, such as an offset of about 45 degrees+/−15 degrees. The hinged connectors and interposed component 110 are substantially rigid to support pronosupination torque from the forearm to the hand without any components loosening or becoming disengaged.

Figure 2:
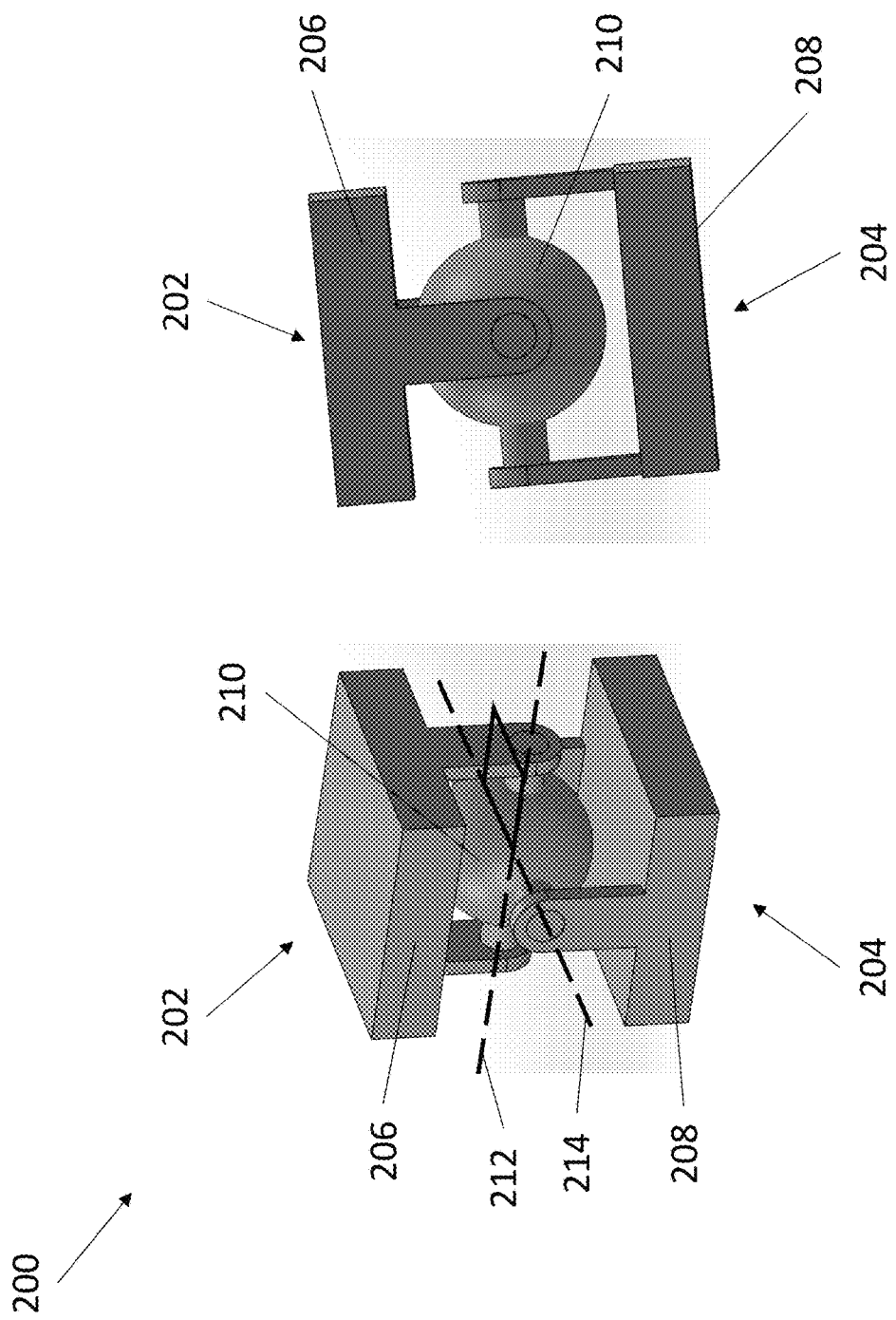
FIG. 2 depicts a prosthetic wrist implant having a bulk structure interposed component.
Figure 5A:
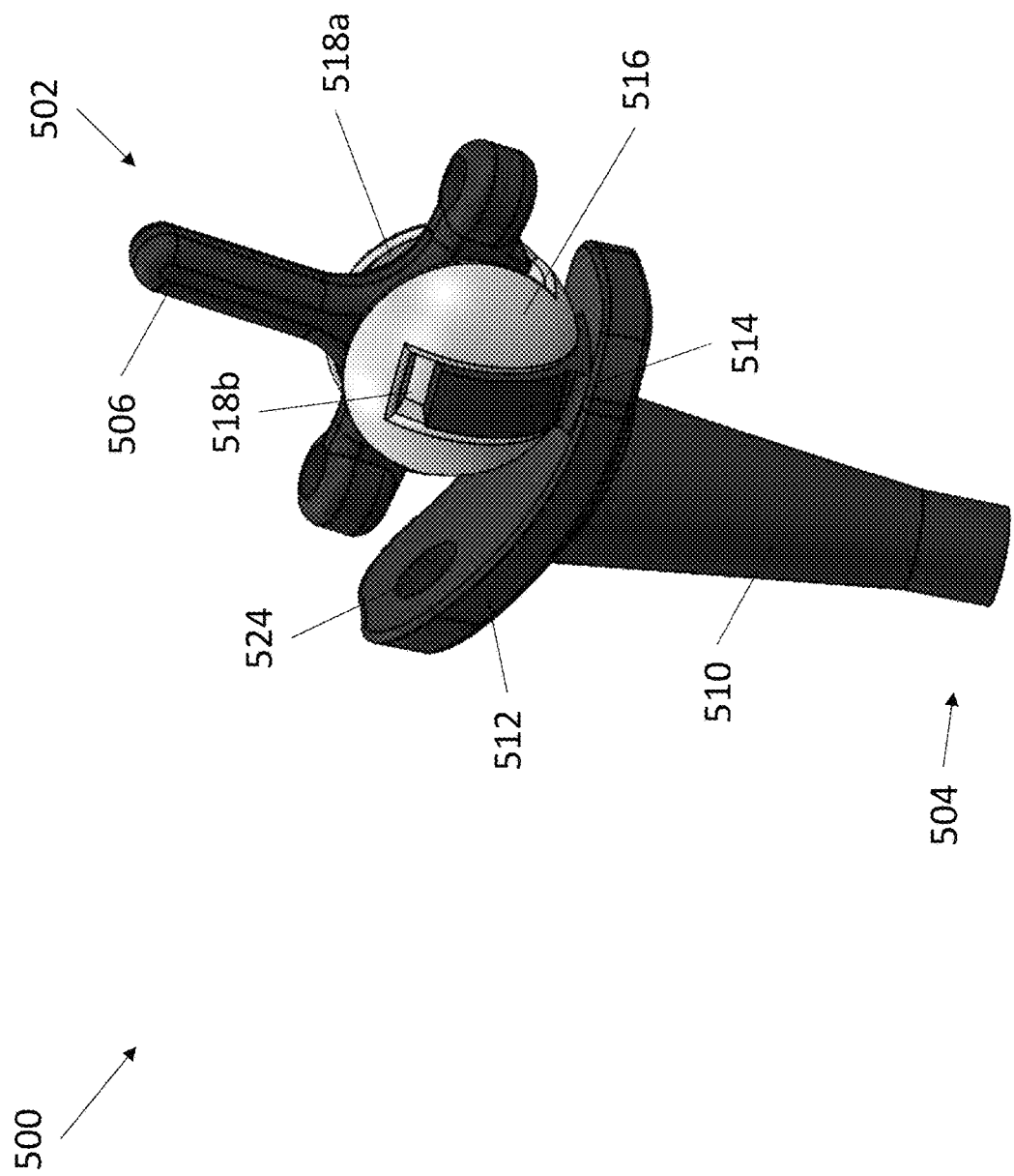
FIG. 5A through FIG. 5D depict another exemplary prosthetic wrist implant.
Figure 5B:
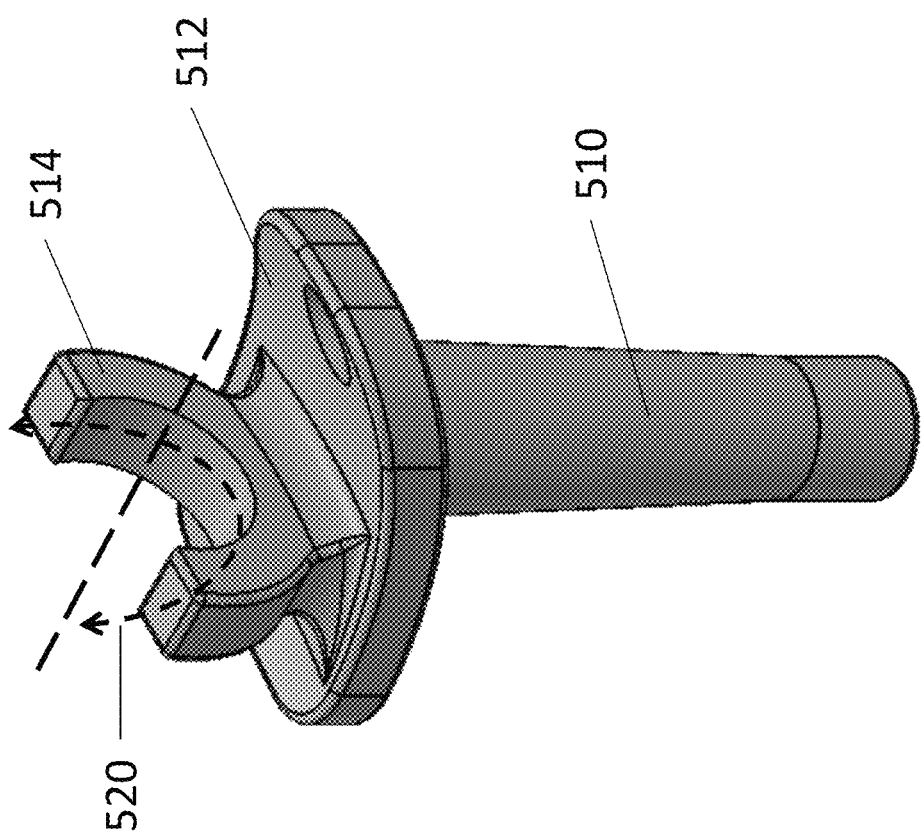
Figure 5D:
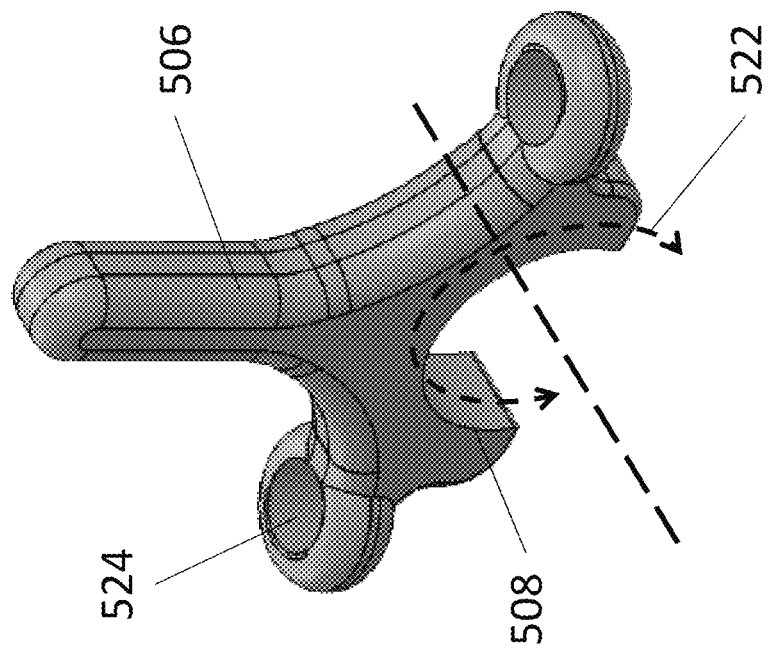
Figure 5C:
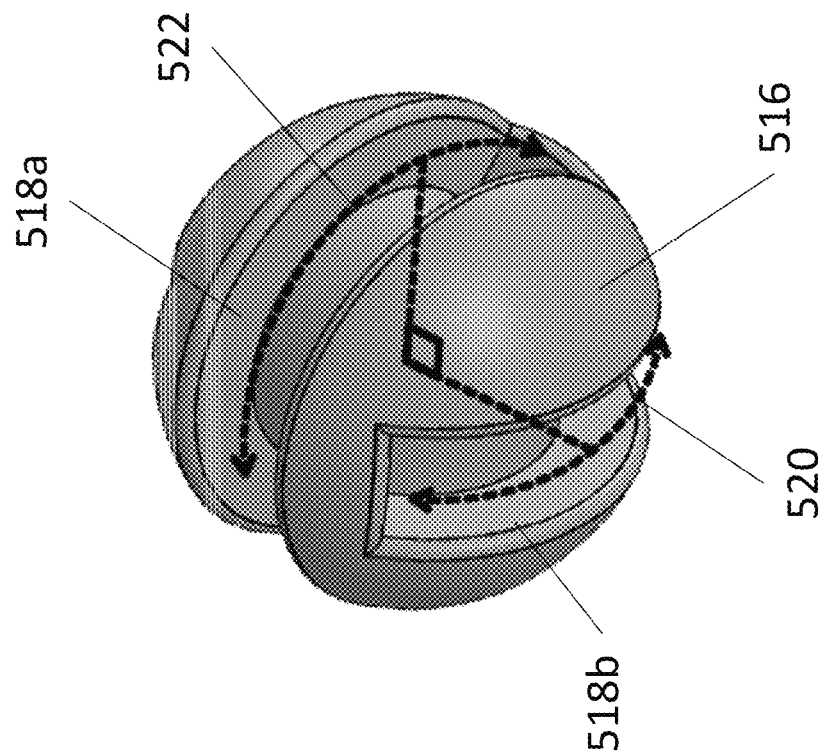

Referring now to FIG. 2A, an exemplary prosthetic wrist implant 200 is depicted. Prosthetic wrist implant 200 has a distal end 202, a proximal end 204, and comprises a carpal component 206, a radial component 208, and a bulk structure interposed component 210. Interposed component 210 substantially occupies the volume of space between carpal component 206 and radial component 208 to maintain the articulating area substantially free of potentially obstructive material. While interposed component 210 can have any desired three-dimensional shape, the embodiment depicted in FIG. 2A has a spherical shape. Similar to wrist implant 100, interposed component 210 of wrist implant 200 is connected to carpal component 206 by a first hinged connection aligned along axis 212 and to radial component 208 by a second hinged connection aligned along axis 214. Axis 212 and axis 214 are orthogonal to each other, and correspond to the wrist's extension to flexion range of motion and ulnar deviation to radial deviation range of motion, respectively. However, it should be understood that implant 200 can be implanted in any suitable orientation, such that the alignment of axis 212 and axis 214 with respect to the wrist's ranges of motion are interchangeable.

In various embodiments, the connection between the interposed components with the carpal components and radial components includes a low wear or low friction bearing, such as a polymer bearing or a polyethylene bearing, to minimize or prevent metal-on-metal contact. The bearing can be sealed to prevent any worn down metal or plastic particles from being exposed to the body. In other embodiments, the entire articulating space of the wrist implants can include an enclosure or casing to prevent any worn down metal or plastic particles from being exposed to the body.

Referring now to FIG. 3A and FIG. 3B, an exemplary prosthetic wrist implant 300 is depicted. Implant 300 has a distal end 302, a proximal end 304, and comprises a carpal component 306, a radial component 308, and a non-articulating interposed component 310. Carpal component 306 and radial component 308 can comprise any suitable number of screw holes for anchoring the components to bone or to another prosthetic structure. Interposed component 310 comprises a first curved piece 312 attached to carpal component 306 and a second curved piece 314 attached to radial component 308. First curved piece 312 and second curved piece 314 can have any suitable geometry, including but not limited to a length having an arced curve or a parabolic curve. First curved piece 312 and second curved piece 314 are attached to each other at their respective vertices. In some embodiments, first curved piece 312 and second curved piece 314 are rigid along the length of their curve and are flexible at the point of attachment at their respective vertices. In other embodiments, first curved piece 312 and second curved piece 314 are flexible throughout, wherein the flexibility of each piece can be varied based upon the material used, the thickness of the material, or combinations thereof. For example, each curved piece 312 and 314 can have a larger thickness at their ends to form a rigid attachment with carpal component 306 and radial component 308, respectively, and each curved piece 312 and 314 can have a graded thickness that gradually decreases up to their vertices to provide increasing flexibility towards the attachment to each other at their respective vertices. In each embodiment, first curved piece 312 is configured to flex at least about axis 318, and second curved piece 314 is configured to flex at least about axis 316, axis 316 and axis 318 being orthogonal to each other and correspond to the wrist's extension to flexion range of motion and ulnar deviation to radial deviation range of motion, respectively. However, it should be understood that implant 300 can be implanted in any suitable orientation, such that the alignment of axis 316 and axis 318 with respect to the wrist's ranges of motion are interchangeable. It should also be understood that the flexible, non-articulating connection between first curved piece 312 and second curved piece 314 is not limited to any particular axis, and can be biased in any desired direction by adjusting the thickness of the material used or the attachment configuration. The interposed component 310 is thereby configured to provide prosthetic wrist implant 300 with freedom of movement including flexion/extension, radial/ulnar deviation, and combinations thereof, while allowing pronosupination torque transfer.

Referring now to FIG. 4A through FIG. 4D, an exemplary prosthetic wrist implant 400 is depicted. Implant 400 has a distal end 402, a proximal end 404, and comprises a carpal component 406, a radial component 410, and an interposed component 414. Carpal component 406 comprises a proximal curved runner 408, and radial component 410 comprises a distal curved runner 412. Carpal component 406 and radial component 410 can also comprise any suitable number of screw holes for anchoring the components to bone or to another prosthetic structure.

Interposed component 414 comprises a solid spherical shape having a first groove 416a and a second groove 416b. Grooves 416a and 416b are each open at their top and embedded into the outer surface of the spherical shape of interposed component 414. Groove 416a is aligned along the curve of a first great-circle, and groove 416b is aligned along the curve of a second great-circle, wherein a plane of the first great-circle and a plane of the second great-circle are aligned orthogonal to each other (dashed lines, FIG. 4C) and correspond to the wrist's extension to flexion range of motion and ulnar deviation to radial deviation range of motion, respectively. However, it should be understood that implant 400 can be implanted in any suitable orientation, such that the alignment of groove 416a and groove 416b with respect to the wrist's ranges of motion are interchangeable. Runner 408 of carpal component 406 is sized and arced to fit within and slide along groove 416a. Likewise, runner 412 of radial component 410 is sized and arced to fit within and slide along groove 416b. In certain embodiments, groove 416a and 416b each has a depth (and runner 408 and runner 412 each has a corresponding height) sufficient to support a pronosupination torque, such as a depth of between about 1 cm and 2 cm. In other embodiments, groove 416a and 416b can each have an overhanging lip along their open tops that partially encloses runner 408 and runner 412, respectively, to enhance the security of fit between the components.

Referring now to FIG. 5A through FIG. 5D, an exemplary prosthetic wrist implant 500 is depicted. Implant 500 has a distal end 502, a proximal end 504, and comprises a carpal component 506, a radial component 510, and an interposed component 516. Carpal component 506 comprises a proximal curved runner 508. Radial component 510 comprises a distal plate 512 and a curved runner 514 attached to plate 512. In this arrangement, runner 514 can be positioned laterally offset from a central long axis of radial component 510. For example, runner 514 can be positioned between about 5 mm and 25 mm offset from a central long axis of radial component 510. Carpal component 506 and radial component 510 can also comprise any suitable number of screw holes 524 for anchoring the components to bone or to another prosthetic structure.

Interposed component 516 comprises a solid spherical shape having a first groove 518a and a second groove 518b. Grooves 518a and 518b are each open at their top and embedded into the outer surface of the spherical shape of interposed component 516. Groove 518a is aligned along the curve of a first great-circle, and groove 518b is aligned along the curve of a second great-circle, wherein a plane of the first great-circle and a plane of the second great-circle are aligned orthogonal to each other (dashed lines, FIG. 5C) and correspond to the wrist's extension to flexion range of motion and ulnar deviation to radial deviation range of motion, respectively. However, it should be understood that implant 500 can be implanted in any suitable orientation, such that the alignment of groove 518a and groove 518b with respect to the wrist's ranges of motion are interchangeable. Runner 508 of carpal component 506 is sized and arced to fit within and slide along groove 518a. Likewise, runner 514 of radial component 510 is sized and arced to fit within and slide along groove 518b. In certain embodiments, groove 518a and 518b each has a depth (and runner 508 and runner 514 each has a corresponding height) sufficient to support a pronosupination torque, such as a depth of between about 1 cm and 2 cm. In other embodiments, groove 518a and 518b can each have an overhanging lip along their open tops that partially encloses runner 508 and runner 514, respectively, to enhance the security of fit between the components.

Figure 6A:
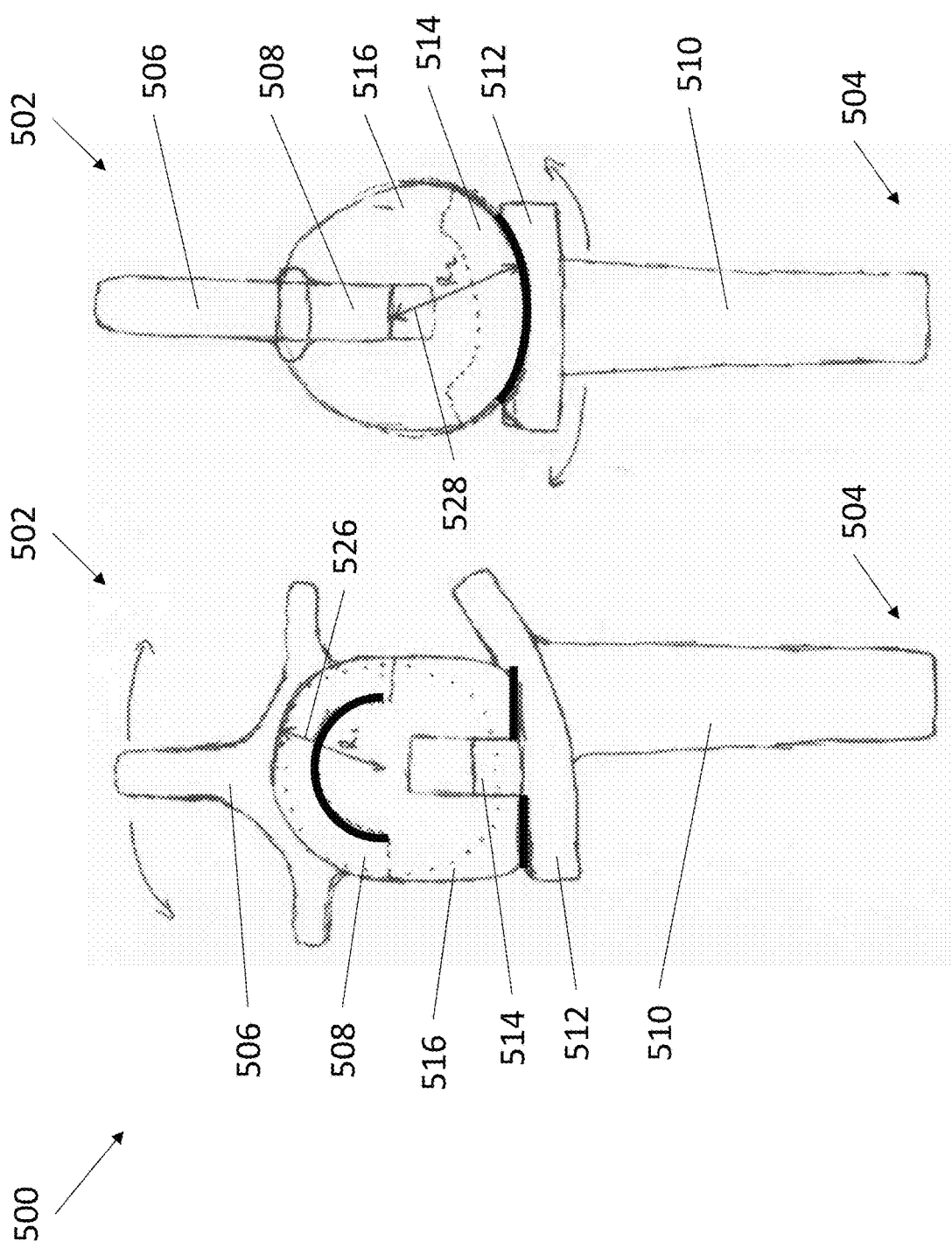
FIG. 6A and FIG. 6B depict another exemplary prosthetic wrist implant.
Figure 6B:
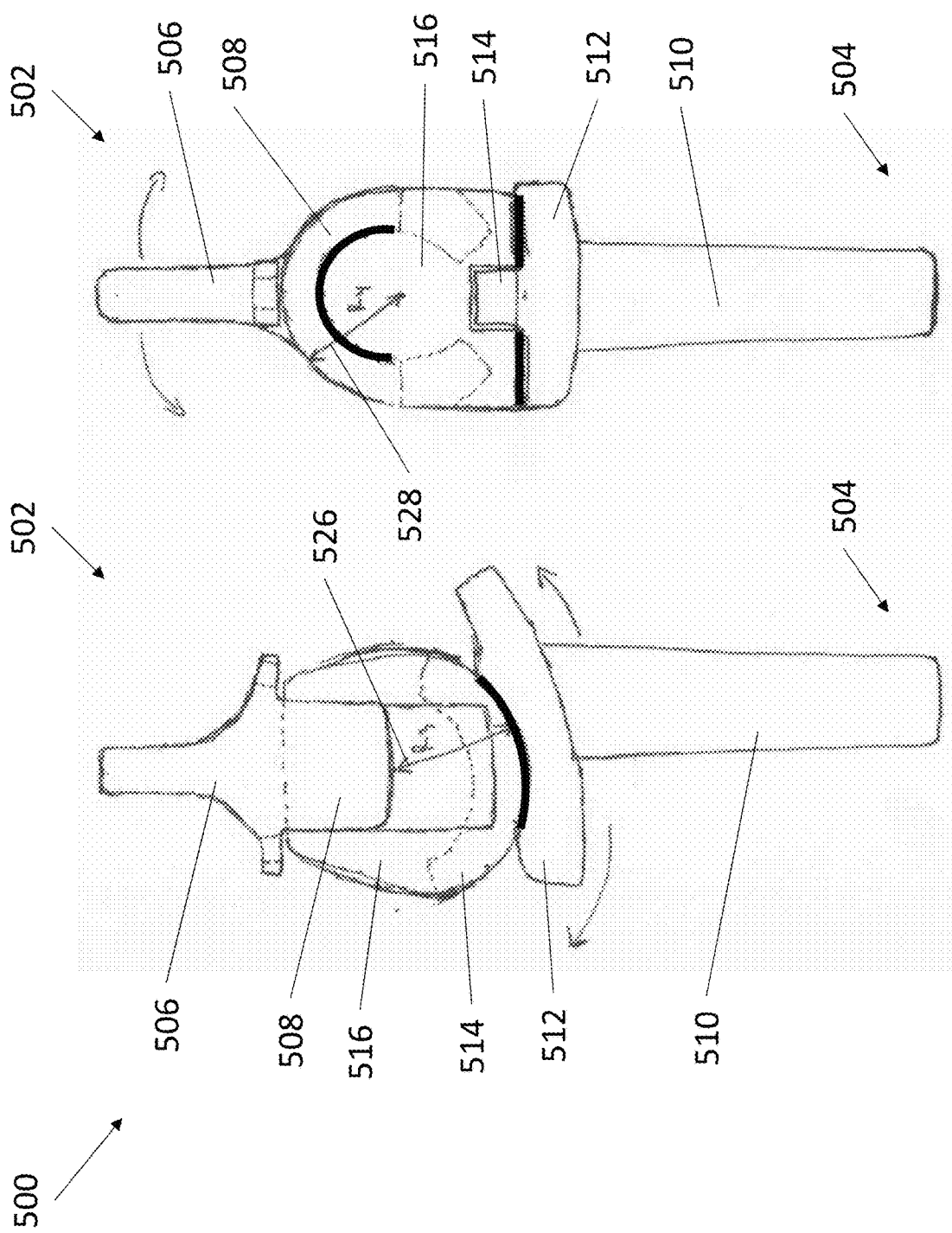

In certain embodiments, implant 500 can be tuned for enhanced fit and mobility. Referring now to FIG. 6A and FIG. 6B, modified implants 500 are depicted. FIG. 6A depicts an implant 500 having a non-symmetrical interposed component 516 that, while substantially spherical, is wider at its proximal end such that interposed component 516 presents a greater surface area contacting plate 512 of radial component 510 (bolded lines indicate articulating load bearing surfaces). A greater contact surface area between interposed component 516 and plate 512 of radial component 510 increases the stability between the two components. Runner 514 of radial component 510 also increases torsional stability even if it is not bearing an axial load. The non-symmetrical interposed component 516 also presents a smaller distal radius and a larger proximal radius. In this manner, runner 508 of carpal component 506 rotates along an axis that is smaller than runner 514 of radial component 510. FIG. In some embodiments, the axis of rotation of runner 508 and runner 514 are orthogonal to each other, similar to the implants described elsewhere herein. In some embodiments, the axis of rotation of runner 508 and runner 514 comprise coinciding centers of rotation, similar to the implants described elsewhere herein. 6B depicts an implant 500 having a non-symmetrical interposed component 516 described in FIG. 6A that is rotated by about 90°. Likewise, runner 508 of carpal component 506 and runner 514 of radial component 510 are also rotated by about 90°.

The various prosthetic wrist implants of the present invention can be implanted into a user's wrist space in any suitable configuration. In some embodiments, an implant of the present invention is implanted such that an interposed component has a center of rotation (that is, the point where the axes corresponding to the wrist's extension to flexion range of motion and ulnar deviation to radial deviation range of motion intersect) aligned with the long axis of a patient's forearm. In some embodiments, an implant is positioned such that the center of rotation is placed at approximately the proximal aspect of a patient's capitate bone. In some embodiments, an implant is positioned such that the center of rotation is placed between the proximal extent of the capitate to ¼ the height of the capitate from its proximal extent. In some embodiments, the axes corresponding to the wrist's extension to flexion range of motion and ulnar deviation to radial deviation range of motion are aligned with the wrist's dart thrower's motion. The dart thrower's motion is a movement in the wrist from radial extension to ulnar flexion and combines flexion/extension with radial/ulnar deviation. Aligning an implant of the present invention with the dart thrower's motion thereby aligns the implant a first axis orthogonally with the radial extension to ulnar flexion direction and aligns a second axis in parallel with the radial extension to ulnar flexion direction. In some embodiments, the first axis is set at approximately 45 degrees+/−15 degrees oblique from the sagittal plane of a patient's hand. In some embodiments, the first axis is aligned with the plane defined by the insertion of the flexor carpi ulnaris and the extensor carpi radialis longus/extensor carpi radialis brevis of a patient's arm.

The various components of the present invention described above can be constructed using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art. In various embodiments, the components can be constructed using a porous or semi-porous structure to encourage osseointegration.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Prosthetic Wrist Implant Prototyping

Figure 7C:
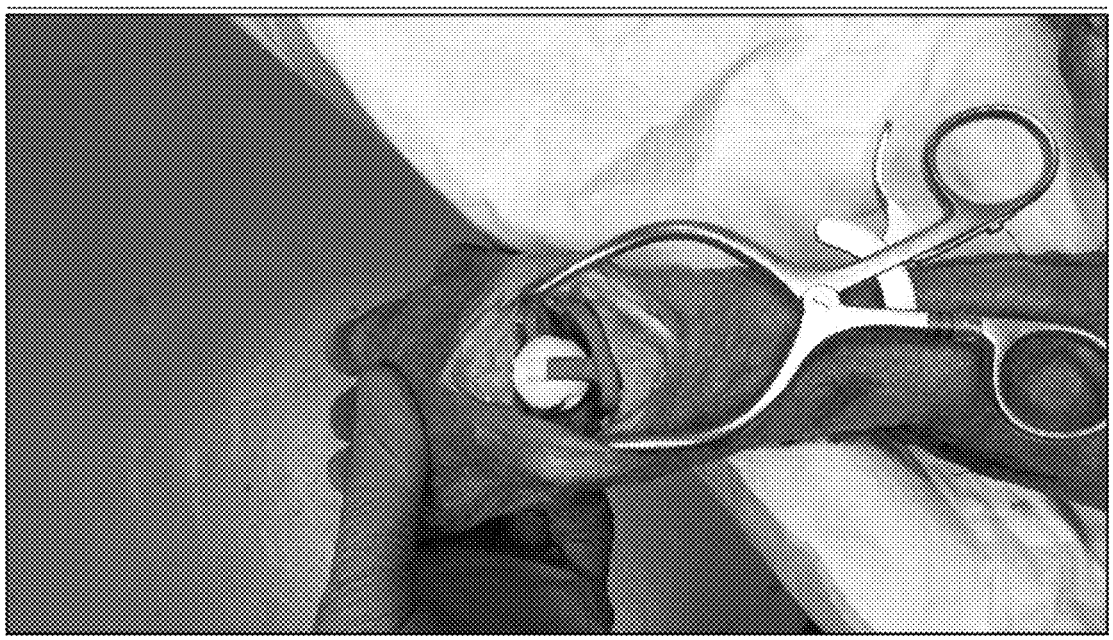
FIG. 7A through FIG. 7C depict the results of experimental examples demonstrating a prototype prosthetic wrist implant.
Figure 7B:
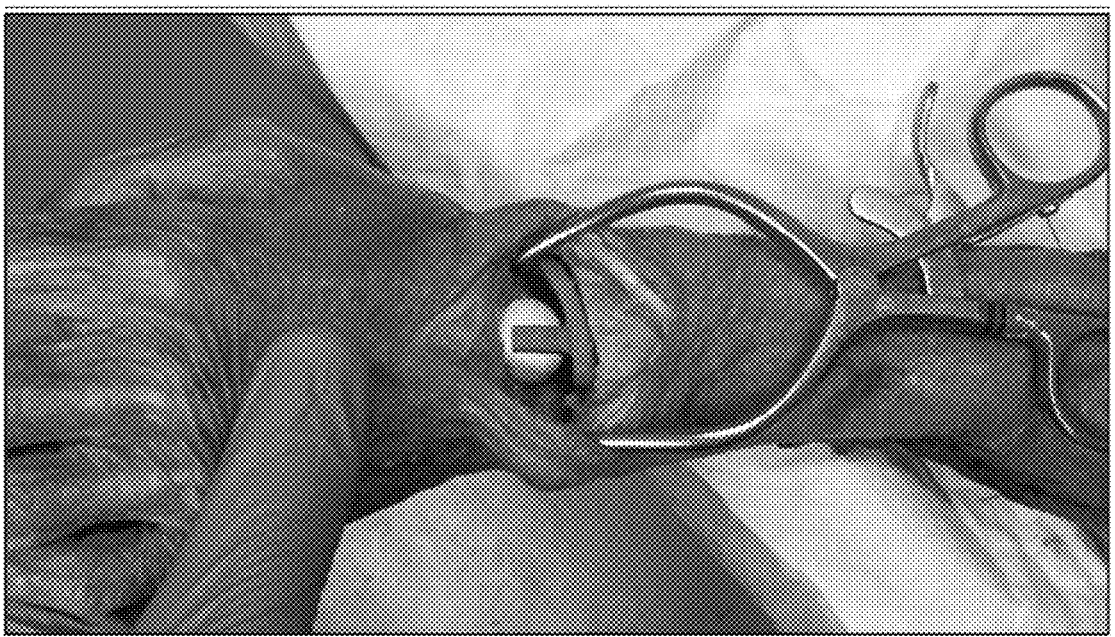
Figure 7A:
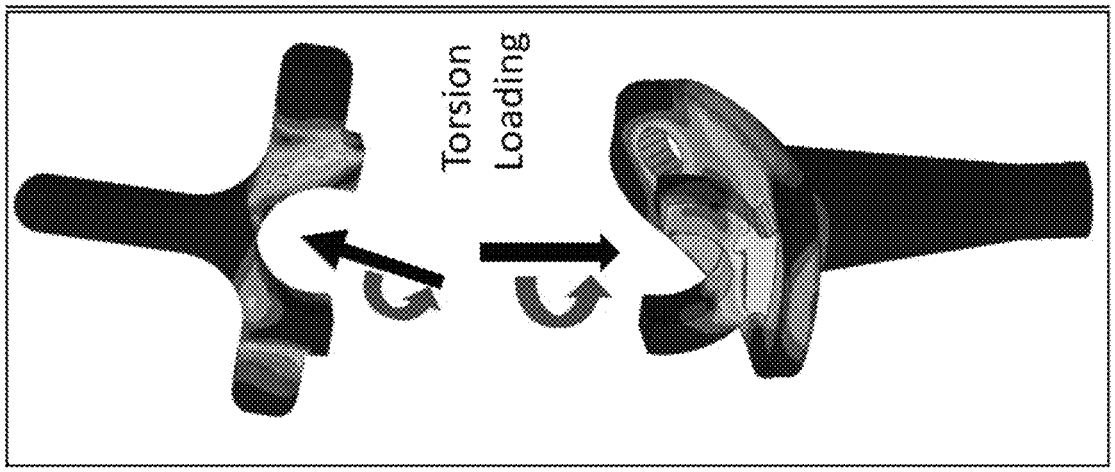

FIG. 7A depicts the results of computational mechanics using finite element analysis. The results show torsion loading in the runners of the carpal and radial components. A prototype wrist implant was 3D printed and implanted into a cadaver wrist (FIG. 7B). The implant was capable of replicating the full range of motion of native wrist (FIG. 7C).

The disclosures of each and every patent, patent application, and publication cited herein are hereby incorporated by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A prosthetic wrist implant comprising:
   a radial component positioned proximal to a carpal component, the radial component having an elongated radial stem extending in a proximal direction configured to attach to a radius bone, and the carpal component having a distal surface configured to attach to one or more carpal bones; and
   an interposed component positioned between the radial component and the carpal component, the interposed component attached to the carpal component by a mobile connection rotatable about a first axis, and to the radial component by a mobile connection rotatable about a second axis, the first axis and the second axis being orthogonal to each other,
   wherein the interposed component comprises a spherical component having a first groove and a second groove embedded on an outer surface of the spherical component, the first groove being aligned along a curve of a first great-circle of the spherical component, the second groove being aligned along a curve of a second great-circle of the spherical component, and wherein a plane of the first great-circle and a plane of the second great-circle are orthogonal to each other.

2. The prosthetic wrist implant of claim 1, wherein the implant has a center of rotation positioned at an intersection of the first axis and the second axis.

3. The prosthetic wrist implant of claim 1, wherein the mobile connections between the interposed component, the carpal component, and the radial component are configured to rigidly support a pronosupination torque.

4. The prosthetic wrist implant of claim 1, wherein the carpal component and the radial component each comprise a runner sized and arced to fit within and slide along the first and second grooves of the spherical component, respectively.

5. The prosthetic wrist implant of claim 4, wherein the runner of the radial component is attached to a distal plate connected to the radial component such that the runner is positioned offset from a central long axis of the radial component.

6. The prosthetic wrist implant of claim 5, wherein the offset is between about 5 mm and 25 mm.

7. The prosthetic wrist implant of claim 1, wherein the first great-circle having a radius that is smaller than a radius of the second great-circle.

\* \* \* \* \*